United States Patent [19]

Sausa et al.

[11] Patent Number: 5,728,584
[45] Date of Patent: Mar. 17, 1998

[54] METHOD FOR DETECTING NITROCOMPOUNDS USING EXCIMER LASER RADIATION

[75] Inventors: Rosario C. Sausa, Bel Air, Md.; Josef B. Simeonsson, Iowa City, Iowa; George W. Lemire, Draper, Utah

[73] Assignee: The United States of America as represented by the Secretary of the Army, Washington, D.C.

[21] Appl. No.: 313,620

[22] Filed: Sep. 30, 1994

Related U.S. Application Data

[60] Continuation-in-part of Ser. No. 220,317, Mar. 30, 1994, which is a division of Ser. No. 028,088, Jun. 11, 1993, Pat. No. 5,364,795.

[51] Int. Cl.[6] .................................................. G01N 33/22
[52] U.S. Cl. ..................... 436/106; 436/110; 436/116; 436/153; 436/172; 73/35.14; 250/282; 250/461.1
[58] Field of Search ..................... 436/116–118, 153, 436/172, 106, 110; 73/35.14; 250/461.1, 282, 287

[56] References Cited

U.S. PATENT DOCUMENTS

| | | |
|---|---|---|
| 3,826,920 | 7/1974 | Woodroffe et al. |
| 4,066,904 | 1/1978 | Bertaux et al. |
| 4,315,753 | 2/1982 | Bruckenstein et al. |
| 4,775,633 | 10/1988 | Roubehler |
| 5,094,815 | 3/1992 | Conboy et al. |
| 5,123,274 | 6/1992 | Carroll et al. |

OTHER PUBLICATIONS

Rodgers et al., "Photofragmentation Laser Induced Fluorescence: a new method for detecting atmospheric trace gases" Applied Optics, vol. 19 No. 21 (1980) pp. 3597–3605.

Mukhtar et al. "Photodissociation of Positive Molecular Ions of Nitrobenzene" Organic Mass Spectrometry, vol. 15 No. 1, (1980) pp. 51–52.

Bunn et al., "Photodissociation of the energy selected nitrobenzene ion" J. Chem. Phys. vol. 84, No. 3 (1986) pp.1424–1431.

Asscher, et al, "Two Photon excitation as a monitoring Technique for Photodissociation Dynamics $CF_3$ No $CF_3+$ BI".

M. Noble, "Photodissociation of Jet–Cooled $(CH_3)_3CNO$: Temporal Separation of Radiationless Transitions Transitions and Unimolecular Reactions".

Simeonsson, et al, "Trace Detection of Nitrocompounds by ArF Laser Photofragmentation/Ionization Spectrometry," 47 Applied Spectroscopy 1907 (Oct. 1993).

Primary Examiner—Jan Ludlow
Attorney, Agent, or Firm—Muzio B. Roberto; Paul S. Clohan

[57] ABSTRACT

A method for the ultra-sensitive detection of atmospheric and surface adsorbed nitrocompounds such as propellants, explosives, and nitro-pollutants employs an excimer (ArF) laser operating at or near 193 nm to photofragment the target molecule and facilitate the detection of the characteristic NO fragment, formed from the dissociation of $NO_2$, by resonance-enhanced multiphoton ionization (REMPI) and/or laser induced fluorescence (LIF) via its A-X, B-X, C-X, and/or D-X electronic transitions. In addition to NO, the detection of other fragments, such as C, CH, $C_2$, NH and OH, by their ionization and/or prompt emission resulting from 193 nm excitation enhances the analyte identification. The analytical utility of this apparatus and method has been demonstrated on a number of compounds including dimethylnitramine (DMNA), nitromethane, nitrobenzene, orthonitrotoluene, para-nitrotoluene and trinitrotoluene (TNT). With the present system, limits of detection in the tens to hundreds of parts-per-billion (ppb) range have been achieved in the gas phase for all of these compounds, using only 1 mJ of laser energy at 193 nm.

5 Claims, 7 Drawing Sheets

| RELATIVE INTENSITIES OF IONS FOR ORTHO– AND META–NITROTOLUENE | | |
|---|---|---|
| m/z | ORTHO (%) | META (%) |
| 30 | 36 | 77 |
| 39 | 31 | 45 |
| 50 | 10 | – |
| 51 | 28 | 100 |
| 65 | 36 | 71 |
| 77 | 100 | 26 |
| 91 | 13 | 77 |
| 92 | 66 | – |
| 107 | 100 | 15 |
| 120 | 9 | – |
| 137 | 3 | 21 |

FIGURE 6

| COMPOUND | LIMIT OF DETECTION (ppm) |
|---|---|
| NO | 1.2 |
| $NO_2$ | 0.50 |
| $CH_3 NO_2$ | 0.18 |
| DMNA | 0.51 |
| NITROBENZENE | 0.49 |
| ORTHO–NITROTOLUENE | 0.12 |
| META–NITROTOLUENE | 0.10 |
| TNT | 0.21 |

FIGURE 7

METHOD FOR DETECTING NITROCOMPOUNDS USING EXCIMER LASER RADIATION

CROSS-REFERENCE TO RELATED APPLICATIONS

This patent application is a continuation-in-part of copending patent application, Ser. No. 08/220,317, filed Mar. 30, 1994, which is a divisional of patent application, Ser. No. 08/028,088, filed Jun. 11, 1993, now U.S. Pat. No. 5,364,795, the disclosures of which are incorporated herein by reference.

GOVERNMENT INTEREST

The invention described herein may be manufactured, used and licensed by or for the U.S. Government without payment to us of any royalty thereon.

BACKGROUND OF THE INVENTION

The present invention relates to a method for detecting trace amounts of nitrocompounds. It provides a novel means for in situ detection of the presence of $NO_x$-containing compounds, wherein x is greater than or equal to one, in the atmosphere or on various surfaces. The invention has been developed in order to monitor the presence of energetic materials, such as propellants and explosives, and nitro-pollutants in various environments.

Detection and monitoring of trace amounts of energetic materials is critical to the security and safety of the population. It is of particular interest in the areas of detecting potential terrorist activity, demilitarization and mine countermeasures. As a result of interest in this area, numerous methods and devices have been developed to reduce the risk to the general population by detecting the presence of such materials and preventing their use. The techniques which have been previously developed and employed are summarized in an article by A. Fainberg, entitled "Explosives Detection for Aviation Security," 255 *Science* 2531 (March 1992).

The techniques previously employed include X-ray detection and nuclear techniques, such as thermal neutron analysis and nuclear resonance absorption. The nuclear techniques monitor the nitrogen content of the unknown sample of energetic material. These techniques have been found to be applicable in the sensing of concealed energetic materials found in luggage or other containers. However, it is extremely difficult to detect the presence of dangerous chemicals—i.e. explosives—when carried by a person. Due to the health risks in exposing a human to x-rays and nuclear techniques, authorities are unable to monitor people in the same fashion or as thoroughly as they can luggage or other containers.

The above described prior art techniques are used to physically detect the presence of the target compounds. However, other prior art methods do exist which serve the purpose of detecting the presence of the target compounds' vapors in the atmosphere. Among the prior art vapor sensing techniques employed are gas chromatography (GC) with chemiluminescent detection, quadrupole mass spectrometry, ion mobility spectrometry (IMS), canine (animal) detection, and laser-based detection.

Although these techniques appear attractive since they are capable of atmospheric vapor analysis, their applications are limited. For instance, when one employs the sensing method of GC-chemiluminescence, the response time before the results are obtained is typically on the order of minutes and is not practical for large scale applications, i.e., baggage inspection at a busy airport. Quadrupole mass spectrometry is limited in its relatively slow time response due to its mass sweep rate (approximately 100 amu/sec). IMS is extremely sensitive (parts per trillion (ppt) range) and has a relatively short response time (seconds); however, it is not quantitatively as accurate as the others since the signal dependence on concentration is non-linear, particularly in the tens of parts-per-billion (ppb) range. Moreover, with IMS, clustering of the target molecules with water, competition for protonation with contaminants, and low mass spectroscopic resolution are problems frequently encountered.

Canines have also been employed for detecting atmospheric vapors of energetic materials. The dog is the original vapor detector, or sniffer. Authorities still use dogs to sweep buildings and sniff luggage or parcels to assure the absence or detect the presence of explosives therein. The use of dogs for these purposes is limited due to the fact that they are subject to fatigue, behavioral variations (good days/bad days) and the need for reinforcement and retraining. Therefore, although canines provide very sensitive vapor detection, the fact that they are subject to various external factors makes it critical to develop an efficient technological method for detecting specific vapors that overcomes the drawbacks of prior art detection methods.

An improved method for detecting the presence of the specific materials of interest in atmospheric vapors was reported in an article by G. Lemire, J. Simeonsson, and R. Sausa entitled, "The Monitoring of Vapor-Phase Nitrocompounds Using 226 nm Radiation; Fragmentation with Subsequent NO Resonance-Enhanced Multiphoton Ionization Detection," 65 *Analytical Chemistry* 529 (1993). In the article, limits of detection for various nitrocompounds were reported using a line tunable, narrow band (approximately 0.2 cm$^{-1}$), frequency-doubled dye laser system with an energy output of approximately 100 µJ/pulse. The laser beam was tuned to 226 nm and was used to photolyze the target molecules and to facilitate the detection of the NO fragment via its $A^2\Sigma^+(v'=0)$-$X^2\pi(v''=0)$ (hereinafter "A-X") electronic transition employing laser-induced fluorescence (LIF) and resonance-enhanced multiphoton ionization (REMPI) methods.

SUMMARY OF THE INVENTION

It is a primary object of the present invention to improve the sensitivity of a laser-based detection apparatus for monitoring and detecting the presence of trace amounts of nitrocompounds present in atmospheric vapors and/or absorbed onto various surfaces by using a laser source operating at a wavelength to photofragment a target molecule and facilitate detection of a characteristic NO fragment by REMPI via its $C^2\pi$-$X^2\pi$ (hereinafter "C-X") and/or $D^2\Sigma^+$-$X^2\pi$ (hereinafter "D-X") electronic transitions, and/or by LIF via its C-X, D-X, A-X and/or $B^2\pi$-$X^2\pi$ (hereinafter "B-X") transitions.

It is another object of the present invention to photofragment a nitro-containing molecule using an excimer laser operating at or near 193 nm and to detect the characteristic NO fragments and other fragments, such as carbon (C), CH, $C_2$, NH and OH, by ionization and/or fluorescence.

It is a further object of the present invention to utilize an excimer laser operating at or near 193 nm for detecting the presence of nitrogen dioxide, dimethylnitramine, nitromethane, nitrobenzene, ortho-nitrotoluene, para-nitrotoluene and trinitrotoluene by monitoring the presence of $NO_x$ in the atmosphere or adsorbed on a substrate.

Still a further object of the present invention is to provide a rugged and mobile laser-based detection apparatus for monitoring and detecting the presence of trace amounts of nitrocompounds present in atmospheric vapors and/or absorbed onto various surfaces.

The present invention is generally characterized in an apparatus and method for real-time monitoring of trace nitrocompounds which may be found in atmospheric vapors and/or adsorbed onto various surfaces by detecting the presence of specific fragments. The instrument employed herein is a rugged and mobile system having a retrieving mechanism, a sample chamber, two detection systems (ion and/or photodetector), and a control and data processing system. The present invention is highly specific to nitrocompounds and can be readily manufactured into a sturdy and fieldable device.

The apparatus herein is employed in the following fashion. Traces of atmospheric vapors are sampled using a conventional suction device. Alternatively, adsorbed solid thin films of the compounds may be volatilized by a laser (infrared or ultraviolet) via fiber optic means and then sniffed. The vapors pass through a pulsed valve which facilitates the supersonic expansion of the analyte and the air (carrier gas) within which it is found. The analyte or target molecule, herein represented by R-$NO_2$, is first photolyzed using 193 nm radiation to form $NO_2$, along with its corresponding companion radical, R. After photolysis, the $NO_2$ fragment is detected by monitoring its predissociative product NO using REMPI and/or LIF via its A-X, B-X, C-X and/or D-X transitions. Thus one laser operating at 193 nm can be used for parent photofragmentation and fragment detection. The 193 nm radiation is also used to excite other fragments such as C, CH, $C_2$, NH, etc., which aid in the identification of the analyte.

More specifically, with reference to the laser fragmentation and detection described, the characteristic NO fragment is excited with the same 193 nm radiation via a single or two-photon process. The excitation process results in either fluorescence, ionization, or both. The fluorescence signal is detected with a photomultiplier tube (PMT) or optical multichannel analyzer (OMA), while the $NO^+$ ions are monitored by a conventional multichannel plate ion detector (MCP). The MCP detector may be employed with a time-of-flight mass spectrometer (TOFMS) to detect the $NO^+$ as well as ions resulting from other fragments. The NO fluorescence and other fragment emission is detected with a photomultiplier tube or optical multichannel analyzer coupled to a monochromator or appropriate interference filters. The resulting signals are displayed and monitored in real-time via a digital oscilloscope. A computer may be employed to store, analyze, acquire date, and/or display the same.

Central to the present invention is the excimer laser which operates at or near 193 nm. The excimer laser serves multiple functions. First, it is used to photodissociate the target molecule into $NO_2$ and its companion radical; second, it facilitates the detection of the characteristic fragment NO by resonance-enhanced multiphoton ionization (REMPI) and/or laser induced fluorescence (LIF) via its A-X, B-X, C-X, and/or D-X electronic transitions; and third, it facilitates the detection of other fragments, such as C, $C_2$, CH, NH, and OH, etc., by ionization and/or fluorescence. The use of 193 nm radiation offers several advantages over the 226 nm radiation. These advantages are: (1) The target molecules are fragmented more efficiently since the molecule's absorption cross-section increases with shorter wavelengths (higher frequency); (2) The high energy output (approximately 300 mJ/pulse) is better suited for single or multiple photon fragmentation of the target molecule and the multiphoton excitation of the NO fragment; and (3) The broad linewidth of the laser, approximately 100 $cm^{-1}$, samples more states of the NO fragment, thus resulting in a lower limit of detection. In addition, the excimer laser is more rugged, compact, and simpler than the dye laser since it does not require dyes, multi-optic components, second harmonic generator, or pump laser.

The present invention has been demonstrated on a number of nitrocompounds such as $NO_2$, dimethylnitramine (DMNA), nitromethane, nitrobenzene, ortho-nitrotoluene, para-nitrotoluene, and trinitrotoluene (TNT) and the results of investigations using the apparatus and method of the present invention are reported in an article by Simeonsson, Lemire and Sausa, entitled "Trace Detection of Nitrocompounds by ArF Laser Photofragmentation/Ionization Spectrometry," 47 *Applied Spectroscopy* 1907 (1993), the contents of which are incorporated herein by reference.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENT

The detection and monitoring of trace amounts of atmospheric vapors of military/security interest is a technological task of increasing significance. The present invention relates to the ultra-sensitive detection of these types of vapors, and specifically the vapors of atmospheric and surface adsorbed $NO_x$-containing compounds. These are compounds which include energetic materials, such as propellants and explosives, and nitro-pollutants.

Many molecules, including energetic materials, are difficult to detect spectroscopically using ultraviolet-visible (UV-Vis) absorption or emission. The difficulty stems from the lack of distinguishing structure or the absence of any features in the UV-Vis spectral region. As a result, numerous other approaches have been sought to overcome this obstacle. One of the successful approaches resulting from experimentation was found to involve the use of laser sensor technology to photodissociate the parent molecules into characteristic fragments. These photofragments typically included di- and triatomic species as well as single atoms which were then found to be readily identifiable in the UV-Vis spectral region.

Common to most energetic material and nitro-pollutants is the $NO_2$ functionality which is easily removed by radiation in the 190–250 nm region of the UV spectrum. It is this moiety which is responsible for a weak and structureless absorption feature observed in the UV region. Ultraviolet laser photodissociation of nitrocompounds, under collision-free conditions, results in the production of $NO_2$ in the initial step of the photolysis. The $NO_2$ molecule can itself be detected or, in accordance with the present invention, further fragmented to form NO which is detected with a high degree of sensitivity and selectivity by REMPI and/or LIF via its A-X, B-X, C-X, and/or D-X transitions. Thus one can employ a single laser, in this case an ArF excimer laser, operating at 193 nm to perform parent photofragmentation and fragment excitation. Additionally, use of 193 nm radiation excites other fragments such as C, CH, $C_2$, CH, NH, OH, etc., which aid in the identification of the parent molecule.

Figure 1:
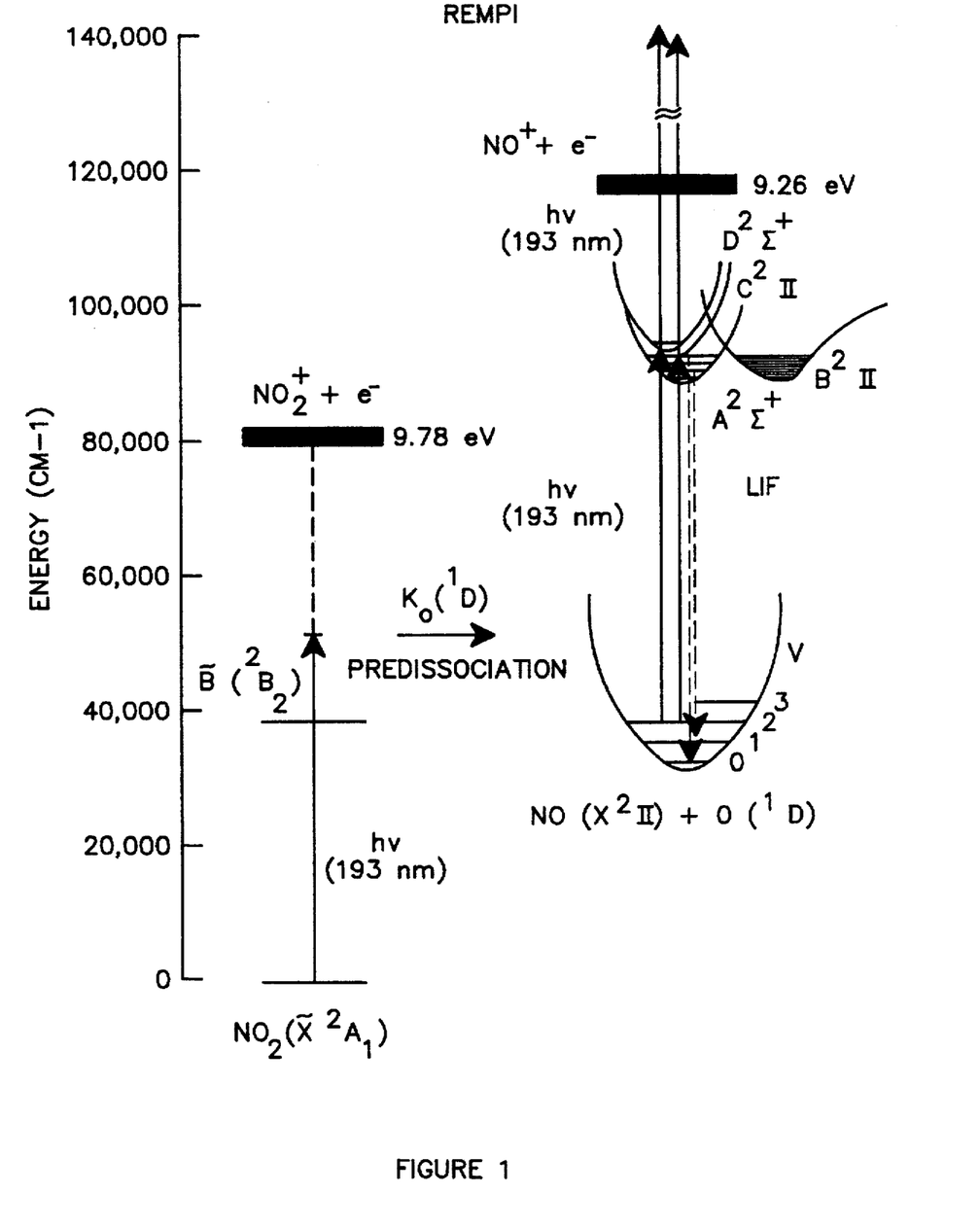
FIG. 1 is a potential energy diagram of $NO_2$ and NO showing the resonance-enhanced multiphoton ionization (REMPI) and laser-induced fluorescence (LIF) scheme employed for the detection of an NO photofragment at 193 nm.

FIG. 1 illustrates the potential energy level diagrams for $NO_2$ and NO. The vertical axis to the left of FIG. 1 represents energy input (i.e., hv in the case of a laser) and is measured in $cm^{-1}$. The diagrams positioned to the right of the vertical axis indicate the various energy levels corresponding to respective electronic states of the $NO_2$ and NO molecules. The energy levels at which $NO_2$ achieves its respective electronic states are shown as horizontal lines. A horizontal line at zero energy corresponds to the electronic ground state $(\tilde{X}^2A_1)$ of $NO_2$. The electronic excited $\tilde{B}(^2B_2)$ state for $NO_2$ is achieved at an energy level of about 40,000 $cm^{-1}$, and at about 80,000 $cm^{-1}$ ionization potential is reached, producing an $NO_2^+$ ion and an electron $e^-$. Absorption by the $NO_2$ of a single photon at 193 nm can result in predissociation of the $NO_2$ to produce an NO fragment, as shown by the horizontal arrow Joining the energy level diagrams of $NO_2$ and NO, at an energy level of about 50,000 $cm^{-1}$.

The electronic states of NO are shown as curves (frequently referred to as potential wells) and are labeled $X^2\pi$ for the ground state, and $A^2\Sigma$, $B^2\pi$, $C^2\pi$, and $D^2\Sigma^+$ (hereinafter A, B, C and D, respectively) for the other electronic states. Although the horizontal arrow symbolizing predissociation leads from the $NO_2$ energy diagram to the ground state X for NO, the NO could also be formed in one of the excited states, A, B, C or D directly from the $NO_2$ or the target compound by the absorption of multiple photons. Horizontal lines intersecting the respective ground or electronic state curves are labeled 0, 1, 2, 3, etc., and represent various vibration states of the NO within each ground or electronic state. Movement between electronic states is indicated symbolically by arrows, with solid arrows representing transitions to a higher energy state and broken arrows representing a drop to a lower state, typically resulting in fluorescence. At about 9.26 eV the ionization potential for NO is reached and an $NO^+$ ion and an electron $e^-$ are produced. Photofragmentation, along with ionization and fluorescence, can occur substantially simultaneously (i.e., within picoseconds) and, therefore, a single laser may be used to photodissociate the target nitrocompound molecule and to characterize the NO fragment using appropriate detectors for monitoring fluorescence and ionization of the NO.

The physical processes underlying the detection of NO, $NO_2$ and other nitrocompounds in accordance with the present invention may thus be understood by reference to FIG. 1. In the present invention, the target molecule, $R\text{-}NO_2$, is first photolyzed to $NO_2$ in both ground and electronically excited states along with its corresponding companion radical, R, via the process $$R-NO_2 \xrightarrow{h\nu}_{193\ nm} R + NO_2(\tilde{X}^2A_1, \tilde{A}^2B_2, \text{and/or } \tilde{B}^2B_2) \quad (1)$$

The NO fragment produced from both ground and electronically excited $NO_2$ is then detected by monitoring its predissociative product NO using REMPI via its A-X (3,0), B-X (7,0) and D-X (0,1) bands at 193 nm, and/or LIF via its A-X, B-X, C-X, D-X, and/or any other electronic bands. Other fragments, such as C, $C_2$, CH, NH and OH, etc., originated from the companion vadical, R, can also be monitored by fluorescence and/or ionization thus aiding the identification of the target molecule. Since a single laser operating at 193 nm can induce substantially simultaneous dissociation of the target nitrocompound molecule and electronic transitions of NO and other fragments, it can be used both for parent photofragmentation and fragment detection. The present invention may additionally be employed where other vibronic A-X, B-X, C-X, and/or D-X bands of NO are used, such as (n,m) bands, where n and m are integers greater than or equal to one designating respective ground and electronically excited vibrational states.

Figure 2:
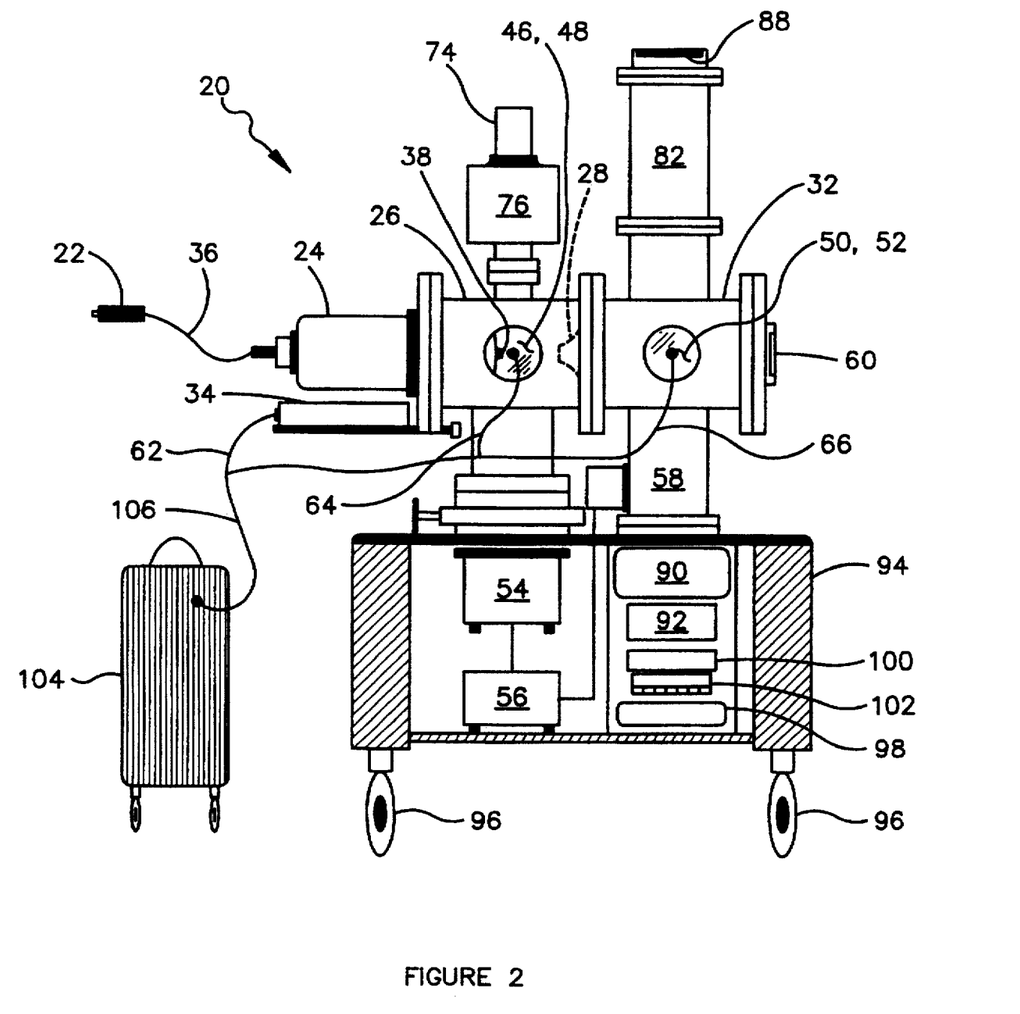
FIG. 2 is a schematic diagram of the analyzer apparatus of the present invention.
Figure 3:
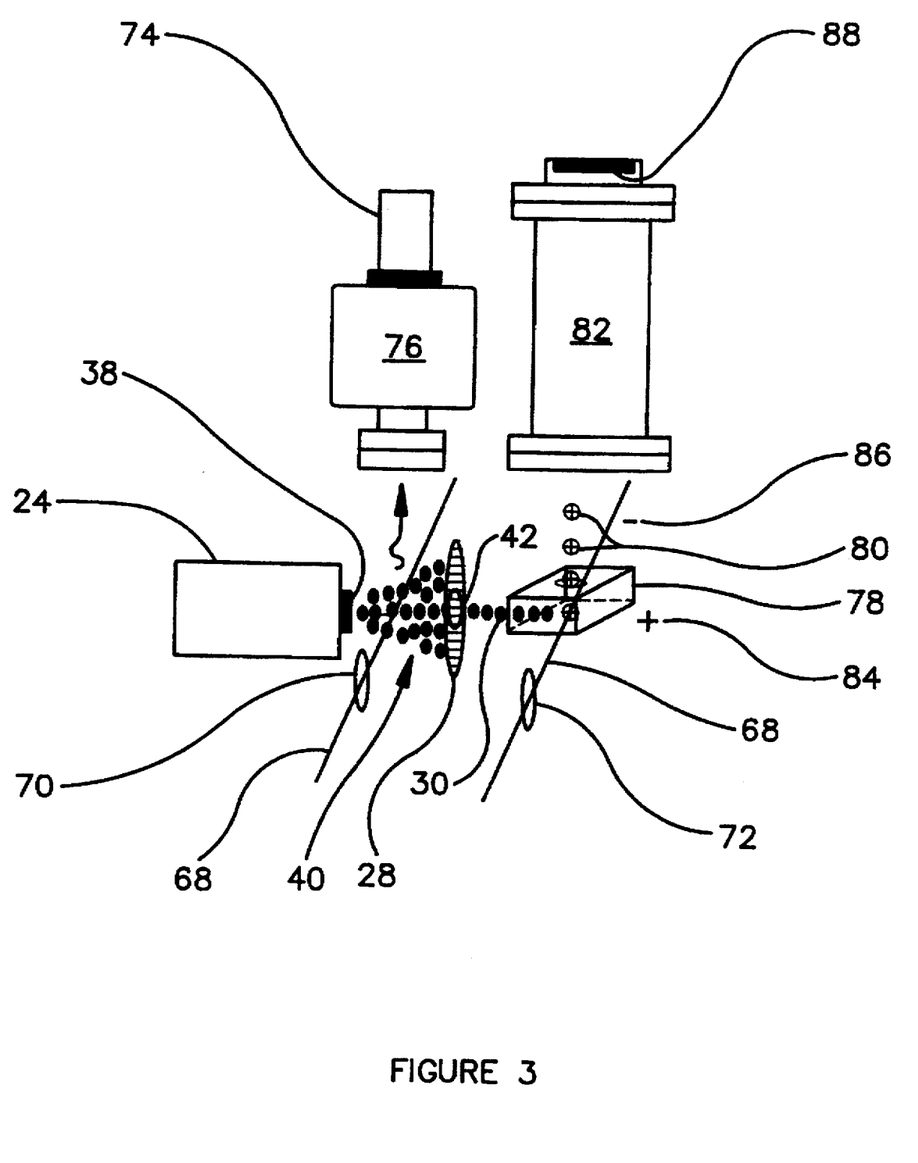
FIG. 3 is a detailed schematic of the optical system employed in the analyzer apparatus of FIG. 2.

An apparatus 20 for detecting nitrocompounds, as shown in FIGS. 2 and 3, includes a suction device 22 for obtaining a sample of atmospheric vapors (i.e., air and analyte mixture), a pulsed valve 24 for supersonically expanding the vapor into an optical analysis chamber 26, a skimmer 28 for producing a molecular beam 30, a mass spectrometric analysis chamber 32 for receiving the molecular beam, and a laser 34 operating at 193 nm for irradiating the vapor within analysis chambers 26 and 32. Suction device 22 is conventional and includes tubing or a hose 36 for being coupled with the pulsed valve 24. The pulsed valve 24 (e.g., pulsed valve by R. M. Jordan & Assoc., Grass Valley, Calif.) supersonically expands the vapor through a small-orifice nozzle 38 to form a diverging molecular flow 40 within optical analysis chamber 26. Skimmer 28 is located downstream of the diverging flow 40 about 2 cm from nozzle 38 and is generally cone shaped with a central aperture or opening 42 having a diameter of about 3 mm to form a molecular beam 30 directed toward the mass spectrometric analysis chamber 32.

Analysis chambers 26 and 32 are shown as cylindrical pressure (vacuum) vessels mounted end-to-end to form a longitudinally extending test section. Ports 46 and 48 are formed on front and rear surfaces of the optical analysis chamber 26 (i.e., parallel to the plane of the figure) and covered with $MgF_2$ windows, for example, for access by the laser beam to irradiate the target molecules. Similar ports 50 and 52 are formed in the mass spectrometric analysis chamber 32. A turbomolecular pump 54 (e.g., the 1000 liter/sec Turbo-vac 1000 of Leybold-Heraeus, Brewster, N.Y.) is coupled to a rotary vane pump 56 and connected with the optical analysis chamber 26 to evacuate the chamber and maintain an average pressure of about $10^{-4}$ Torr. The mass spectrometric analysis chamber 32 is evacuated by a similar turbo pump 58 (e.g., 300 liter/sec) also coupled with rotary vane pump 56 to maintain an average pressure of about $10^{-6}$ Torr. Another port 60 is formed downstream of the molecular beam 44 in an end wall of mass spectrometric analysis chamber 32 and can also serve as an access for the laser, etc., for example when in-line or colinear irradiation of the molecular beam is desired.

The laser 34 is preferably a nontunable excimer laser (e.g., a Lambda Physik EMG 150C) with an unstable resonator operating at or about 193 nm with ArF. Laser beam 68 is transmitted via a main fiber optic cable 62 and is split using a beam splitter (not shown) or the like into a pair of cables 64 and 66 which carry the beam 68 to ports 46 and 50, respectively. UV-quality quartz lenses 70 and 72 (e.g., about 250 mm in diameter) can be used to focus and direct the beams emerging from cables 64 and 66, for example into 10 mm diameter beams traversing the molecular path perpendicularly, at an acute angle or head-on through port 60. Pulse energies of the ArF laser are nominally 1–1.5 mJ in the photolysis region with a maximum laser fluency of about $10^{22}$ photons/cm$^2$.

A photon detector 74 such as a photomultiplier tube (PMT) and/or optical multichannel analyzer (OMA) is arranged perpendicularly relative to the longitudinal axis of the optical analysis chamber 26 for monitoring fluorescence. The detector 74 is coupled with an interference filter 76, such as a monochromator, disposed intermediate the PMT and optical analysis chamber for separating frequencies of interest. The ionization region 78 within mass spectrometric analysis chamber 32 is of a reflectron type (Wiley-McLaren design) and ions 80 are produced and transmitted into a time-of-flight mass spectrometer 82 by acceleration plates 84 and 86 biased at about 1500 V. The flight tube of the mass spectrometer 82 is oriented perpendicular to the direction of the molecular beam 30. A multichannel plate detector 88 is mounted at an opposite end of the mass spectrometer 82 to monitor the ions. The operation of the pulsed valve and laser is synchronized and controlled using precision delay generators (not shown) (e.g., Stanford Research Systems # DG535). The signals obtained by either the photon or ion detectors are displayed and monitored in real-time on a digital oscilloscope 90 (e.g., 125 MHz LeCroy 9400) interfaced with a laptop PC/AT-type computer 92, which is employed for data acquisition, storage, analysis and display.

The entire apparatus 20 can be carried on a cart 94 having wheels 96 and providing space for storing a printer 98, high-voltage supplies 100 and 102, etc. FIG. 2 also shows a luggage item 104 supported on wheels as being exemplary of a surface for being inspected in accordance with the present invention. A fiber optic cable 106 leads from the main cable 62 and is used to volatize the surface of the luggage 104 in the vicinity of the suction device 22 as will be described further below.

The analyzer 20 is employed in the following manner. Samples of trace atmospheric vapors are "sniffed" using the conventional suction device 22. The sniffed vapors are directed into the pulsed valve 24. Alternatively, adsorbed solid/liquid thin films on surfaces may be volatilized by the same 193 nm radiation 68 via fiber optic cable 106. This newly volatilized vapor may then be "sniffed" in the manner described above. As an aside, thermal charged particle sources, and/or other laser radiation may also be employed to volatilize and/or fragment adsorbed film into the vapor phase.

Pulsed valve 24 (i.e., pulsed valve by R. M. Jordan Co. of Grass Valley, Calif.) serves to supersonically expand the air and analyte mixture (vapor) through small-orifice nozzle 38 into the analysis chambers 26 and 32 for optical and mass spectrometric analysis, respectively. A pulsed valve for effusive sampling may also be employed. The molecular beam is formed by skimmer 28 and travels along the longitudinal axis of mass spectrometric analysis chamber 32 past one of the multitude of ports for evacuation, detection, pressure recording, laser access, etc. In particular, ports 46, 48, 50 and 52 are employed for access by the laser beam to irradiate the target molecules. Prior to analyzing a sample, the optical analysis chamber 26 is pumped out through the bottom by the 1,000 liter per second turbo pump 54 (i.e., Leybold-Heraeus, Turbo-Vac 1000 of Brewster, N.Y.) coupled to rotary vane pump 56, while chamber 32 is pumped out by turbo pump 58, also coupled to the same rotary pump. Other pulsed valves and/or pumping systems may be employed herein.

The target molecules are then photolyzed by the ArF excimer laser 34 at 193 nm. Lens 70 may be employed in order to focus the 193 nm radiation. After photolysis, the characteristic fragments, NO, C, $C_2$, CH, NH and OH, can be excited with the same laser radiation by single or multiphoton processes. The excitation can result in either fluorescence, ionization, or both. The photon detector (i.e., photomultiplier tube 74 and/or an optical multichannel analyzer) is used to monitor the fluorescence emission in chamber 26, while a conventional ion detector (i.e. multichannel plate (MCP) 88), coupled to the time-of-flight mass spectrometer 82, is used to monitor the ion signal. For purposes of demonstration, a time-of-flight mass spectrometer with MCP detector is shown for ion analysis and a photomultiplier tube with monochromator for fluorescence detection. The signals obtained by either the photon or ion detector are displayed and monitored in real-time on digital oscilloscope 90. Computer 92 is employed for data acquisition, storage, analysis and display.

Figure 4:
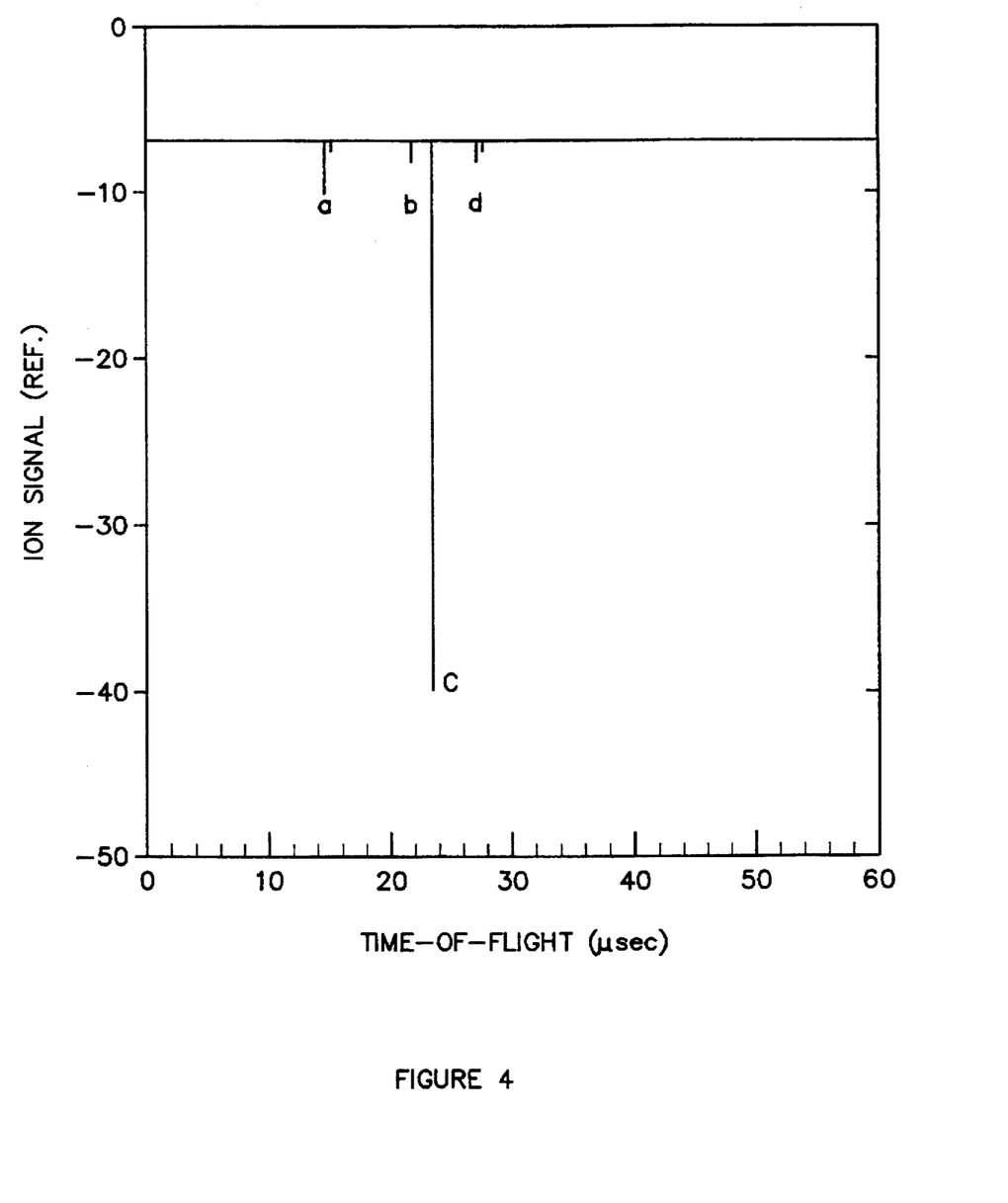
FIG. 4 is a plot of the time-of-flight spectrum of a molecular beam of dimethyl-nitramine sampled from an atmosphere of argon.

FIG. 4 is a TOF mass spectrum obtained when photolyzing various target molecules containing the $NO_x$ moiety—specifically dimethylnitramine (DMNA). The photolyzing occurs in the molecular beam using 193 nm radiation. The molecular beam was obtained by flowing argon gas at approximately one atmosphere over the vapor of the target compound and expanding the resulting gas mixture into the analysis chamber. The spectrum in FIG. 4 reveals two prominent peaks wherein the arrival times to the detector are measured as 14.7 and 23.6 microseconds. Similar observations were obtained when using air or nitrogen as the carrier gas. The mass/charge ration, m/e is obtainable from the following equation, $$m/e = 2V/(L/t)^2 \qquad (3)$$

where V is the acceleration voltage, L is the length of the flight tube, and t is the time-of-flight. The peaks at 14.7 and 23.6 microseconds correspond to a mass/charge ratio (m/e) of 12 and 30 amu, respectively, and are attributed to the $C^+$ and $NO^+$ ion, respectively. The arrival times of the ions may also be obtained by calibrating a known sample. As illustrated in FIG. 4, the $C^+$ (shown at "a") and $NO^+$ peaks (shown at "c") are enhanced as a result of the REMPI process. The mechanism responsible for the latter peak was described above (see FIG. 1). For the C atom case, there exists an unusual spectroscopic situation involving a coincident overlap between the ArF laser output (193 nm) and the fully allowed $^1D_2 - ^1P_0^1$ transition at 193.1 nm. As illustrated in FIG. 4, the 193 nm radiation is resonant with both the C and NO transitions, and as a result, the ionization signals occur virtually at the exclusion of any other species. Peaks labeled "b" and "d" are attributed to $C_2^+$ and $AR^+$ ions, respectively. The selectivity for these fragments is further enhanced by the use of a TOF mass spectrometer, which prevents detection of any spectral ionization interferences, except those which are also isobaric.

Figure 5A:
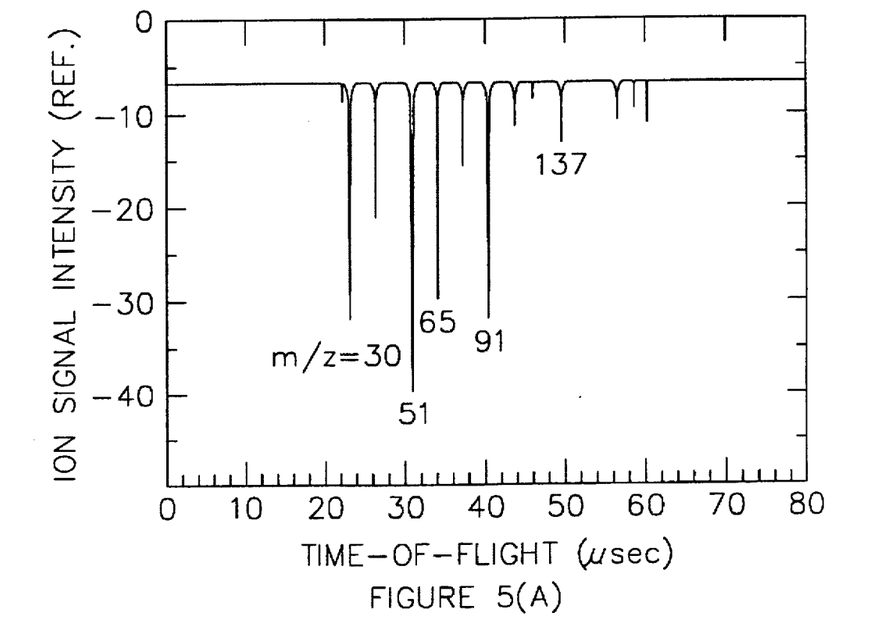
FIG. 5A is a time-of-flight REMPI mass spectrum of orthonitrotoluene and FIG. 5B of meta-nitrotoluene.
Figure 5B:
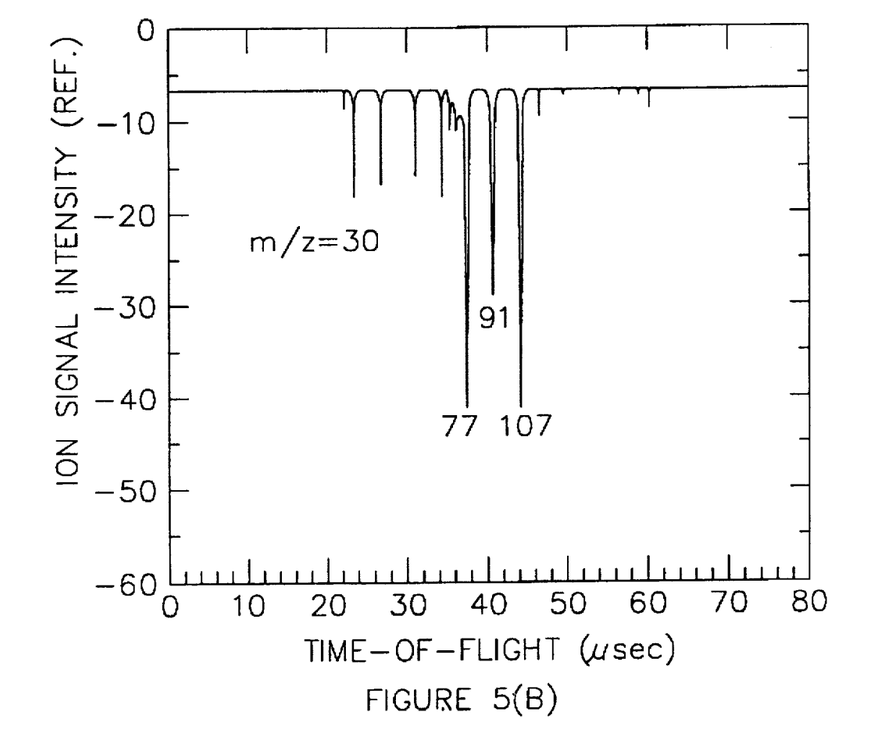
Figure 6:
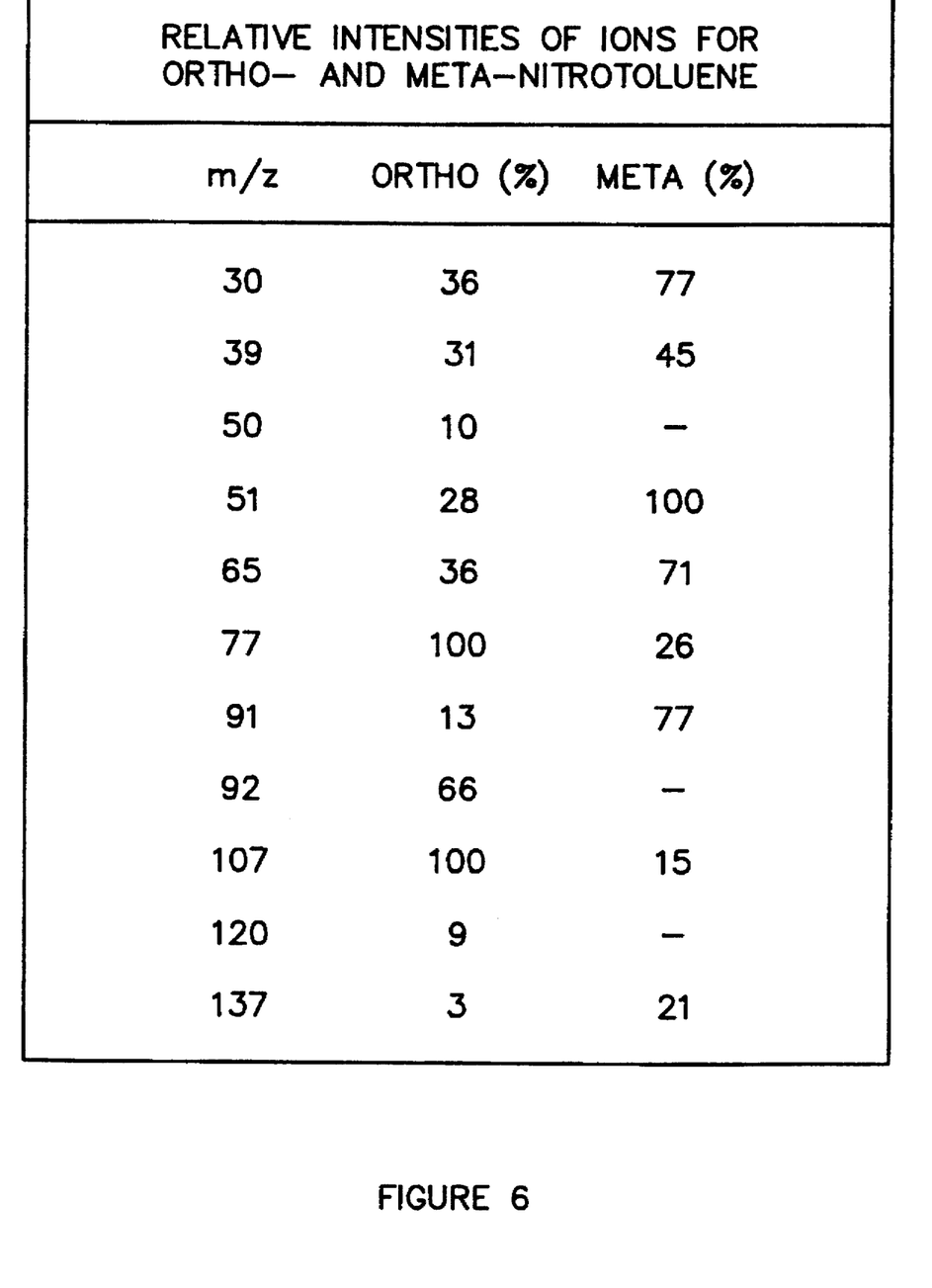
FIG. 6 is a chart of relative intensities of ions for the 193-nm excitation of ortho- and meta-nitrotoluene.

FIGS. 5A and 5B are TOF mass spectra of ortho and meta-nitrotoluene, respectively, illustrating the fragmentation and ionization of the molecules using unfocused 193 nm radiation as the excitation source and effusive sampling. These two molecules produce similar fragments but in different intensity ratios. The 193 nm excited spectra are similar to electron impact spectra, with the exception of enhanced signals for the $NO^+$ species, and can be used to differentiate the two isomers. Relative fragment peak intensities for ortho and meta-nitrotoluene are given in FIG. 6. Readily identifiable masses include m/z=77 (phenyl group), 91/92(tropylium ion or benzyl ion), and 137 (nitrotoluene parent ion), where m is mass and z is charge.

Figure 7:
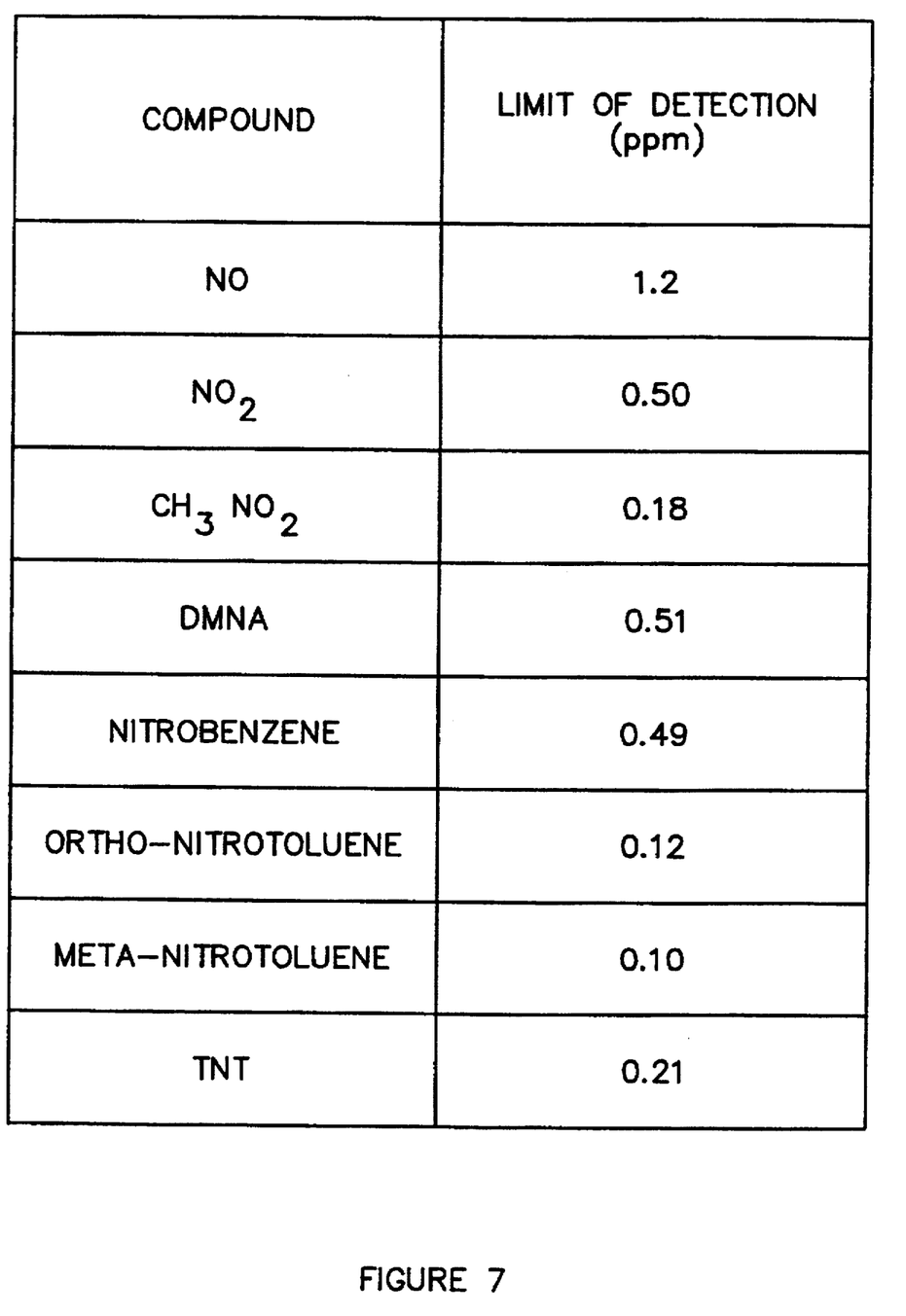
FIG. 7 is a chart which indicates typical limits of detection for various $NO_2$-containing compounds tested employing the apparatus and method of the present invention.

Limits of detection (LODs) were determined for several compounds using the apparatus described herein and are depicted in tabular form in FIG. 7. The limit of detection is defined within the scope of the present invention by the following relationship, $$C_L = 3\sigma/S \qquad (2)$$

where $C_L$ is the concentration (ppb) of the analyte that produces a signal, S (MV/ppb), equal to three times the standard deviation (sigma) of the background when no analyte is present—i.e., introduced through the nozzle. The limits of detection reported in FIG. 7 are based on employing the apparatus of the present invention using approximately 1 mJ of 193 nm radiation and refer to the concentration of the analyte vapor prior to its introduction into the analyzer apparatus.

The LODs set forth in FIG. 7 are estimates and are subject to numerous variables which must be taken into consideration. They depend on a number of factors, such as laser pulse energy, sample introduction efficiency, the voltage settings on the ion optics and detector, and the photodissociation efficiency. All of these factors affect the rate of signal production. Detection limits in the ppb can be obtained with a relatively small amount of laser pulse energy, approximately 1 mJ for these LODs. When the LODs set forth in FIG. 7 were determined, differences in vapor pressures were taken into account. Therefore, any differences observed in FIG. 5 result from differences in the absorption cross sections and photodissociation efficiencies of the steps that lead to the formation of the NO fragment at 193 nm.

The present invention has been shown to be useful; moreover, limits of detection (LODs) for numerous compounds were determined and are reported herein for $NO_2$, DMNA, nitromethane, nitrobenzene, ortho- and para-nitrotoluenes, and TNT (FIG. 7).

From the above, it will be appreciated that the present invention, which encompasses the apparatus as well as the method for accomplishing the detection of the $NO_x$-containing compounds, employs a single laser operating at a frequency suitable to photofragment target $NO_x$-containing molecules and to facilitate the detection of the characteristic NO fragment by REMPI via its C-X and/or D-X electronic transitions and/or by LIF via its A-X, B-X, C-X and/or D-X transitions. More specifically, the invention herein facilitates the detection of the presence of atmospheric vapor of $NO_2$-containing compounds based on the 193 nm photolysis of target molecules. The characteristic NO fragments, formed from the rapid dissociation of $NO_2$, are subsequently detected using the same laser by REMPI and/or LIF via the transitions set forth above. In addition, the 193 nm radiation facilitates the detection of other fragments, such as C, $C_2$, CH, NH and OH, by ionization and/or emission. This enhances the overall selectivity of the system.

The laser photodissociation and fragment detection technique claimed herein is most effective when coupled with pulsed molecular beam or pulsed effusive sampling. The former greatly improves the selectivity over ambient sampling and sensitivity over continuous sampling. The molecules in the molecular beam are colder than those at ambient conditions since they are subject to a supersonic expansion into a vacuum through a pulsed, small-orifice, nozzle. Although the NO fragment is certainly no longer colder, the analytes (the substance whose presence is sought to be determined) are produced in a few distinct ro-vibrational states and, as a result, their absorption spectrum is considerably less congested and easier to analyze. In addition, this procedure minimizes, or eliminates, spectral interferences which may otherwise by present from other molecular rotational bands.

The present invention additionally employs a pulsed nozzle which greatly reduced the total gas throughput entering the analysis chamber while maintaining a high density of the sample gas. Hence, the pumping requirements employed herein are less than for continuous sampling which allows for a more compact design for the apparatus herein.

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

What is claimed is:

1. A method for the detection of atmospheric and surface absorbed $NO_x$-containing compounds comprising the steps of:

(a) isolating said compounds from the atmosphere or surface to which said compounds are absorbed (b) directing said isolated compounds into a sampling chamber;

(c) exposing said isolated compounds within said sampling chamber to a laser beam having a wavelength of about 193 nm to form a characteristic NO fragment and exciting said fragment by subjecting the fragment to the same laser beam at the same wavelength;

(d) detecting said NO fragment using at least one of an ion detector and a fluorescent detector (e) exciting other characteristic fragments with said laser beam;

(f) detecting said other characteristic fragments with at least one of said ion detector and said fluorescent detector; and (g) recording and monitoring the at least one detector on a data acquisition and processing system to detect said $NO_x$-containing compounds.

2. A method in accordance with claim 1 wherein said exposing step includes exciting said NO fragment via at least one of an A-X, B-X, C-X and D-X transition.

3. A method in accordance with claim 1 wherein said exciting step includes exciting at least one of a C, $C_2$, CH, NH and OH species.

4. A method in accordance with claim 1 wherein said detecting step includes utilizing an ion detector in the form of a multichannel plate and/or a fluorescence detector in the form of at least one of a photomultiplier tube and an optical multichannel analyzer equipped with an interference filter.

5. A method of detecting atmospheric and surface adsorbed $NO_x$-containing nitrocompounds comprising:

(a) photofragmenting said $NO_x$-containing compounds to produce NO and other photofragments;

(b) exciting the NO fragment and other produced photofragments by a resonance-enhanced multiphoton ionization process; and (c) detecting said NO fragment and other photofragments by employing at least one of an ion detector and a fluorescence detector wherein said photofragmentation and excitation are are achieved by irradiation using a laser set at approximately 193 nm.

* * * * *